United States Patent [19]
Fowler, Jr.

[11] Patent Number: 5,785,649
[45] Date of Patent: Jul. 28, 1998

[54] SURGICAL RETRACTOR STAY APPARATUS

[75] Inventor: James M. Fowler, Jr., Houston, Tex.

[73] Assignee: Lone Star Medical Products, Inc., Houston, Tex.

[21] Appl. No.: 829,011

[22] Filed: Mar. 31, 1997

[51] Int. Cl.$^6$ .................................................. A61B 17/02
[52] U.S. Cl. .................................. 600/233; 600/217
[58] Field of Search .............................. 600/201, 206, 600/209, 217, 233, 236, 210, 215, 227, 231, 235

[56] References Cited

U.S. PATENT DOCUMENTS

| | | | |
|---|---|---|---|
| Re. 32,021 | 11/1985 | Scott, Jr. | 600/233 X |
| 3,762,401 | 10/1973 | Tupper | 600/217 |
| 4,430,991 | 2/1984 | Darnell | 600/233 X |

*Primary Examiner*—Jeffrey A. Smith
*Attorney, Agent, or Firm*—Pravel, Hewitt, Kimball & Krieger

[57] ABSTRACT

An improved surgical retractor stay has an integrally formed handle body and elongated elastic member with a tail that can engage a slot of a retractor. The improved construction preferably includes an injection molded one piece handle and elongated member so that void spaces are eliminated. A wire hook member includes multiple folded sections that are encapsulated by the handle (e.g., during injection molding of the handle about the hook member). An exposed portion of the hook member extends beyond the distal tip of the handle body and provides a sharp end portion that is used to engage selected body tissue.

28 Claims, 1 Drawing Sheet

SURGICAL RETRACTOR STAY APPARATUS

BACKGROUND OF THE INVENTION

1. Field of the Invention

The present invention relates to surgical retractors and surgical retractor stays. More particularly, the present invention relates to an improved elastic surgical retractor stay and its method of manufacture wherein a handle body is injection molded about a specially shaped needle, and wherein an elastic member is an elongated extension of the injection molded handle.

2. General Background of the Invention

During the course of a surgical procedure or operation, the surgeon opens the patient with a scalpel, forming an incision and surgical site. As the surgeon cuts deeper, the operating room staff typically holds tissue away from the operative field using retractors.

Most retractors are one piece metallic implements that retract a wound in a non-yielding manner. Manipulation and movement of the surgeon as well as movement caused by contracting muscles or tissues of the patient can result in bruising or tearing of tissue.

Once an incision is separated and retracted, there is often a need for multiple stays in the form of sutures for holding various tissues, for example different organs. Elastic surgical retractor systems are in commercial use that include elastic stays, each having an elongated elastic member that is typically a hollow length of elastic tubing. The elastic tubing provides proximal and distal end portions. The distal end portion carries an elongated hook constructed of wire.

The wire hook has a proximal end that is placed in the distal end of the bore of the hollow tubing. A shrink wrap is placed over the hook and tubing to hold the proximal end of the wire hook firmly in position within the bore of the tubing at the distal end. The embedded portion of the wire hook member is usually recurved or folded. This folded proximal portion of the wire hook expands the tubing slightly, forming a vertically extended portion that defines a handle.

Various patents have issued for elastic stay retractor systems. A surgical retractor array system is disclosed in U.S. Pat. No. 4,434,791, issued to W. Dale Darnell on Mar. 6, 1994. This surgical retractor system comprises an array of standardized, interchangeable, annular retractor frame sections of various shapes of which the end portions are configured to permit the interchangeable, hinged connection of the various shaped frames in forming generally annular retractor units adaptable to conform to fit the surface contours of various patients upon which a surgical operation is to be performed. This retractor frame is designed to accept yielding rubber or like elastic stays.

Other recent patents have issued that relate to elastic type retractor stays and related retractor frames and systems.

U.S. Pat. No. 4,274,398, issued to Frank B. Scott, Jr., issued Jun. 23, 1981, discloses a surgical retractor which includes an annular frame conformed to fit the surface contour of the portion of the body to be operated on. At least one stay includes an elastic member and a tissue holding hook. The frame has a plurality of notches spaced about its periphery. The elastic portion of the stay is in the form of a length of hollow elastic tubing adapted to be inserted into one of the notches of the frame and held in place by friction to retract the tissue. The hook is a single, curved wire member. It has a folded proximal end that fits the hollow bore of the elastic tube.

U.S. Pat. No. 4,430,991, issued to W. Dale Darnell, issued on Feb. 14, 1984, discloses a surgical retractor stay with a single tissue holding hook affixed to the elastic hollow tubing member of the stay by a retaining member. The retaining member has a body in which the hook shank is embedded with the sharp end of the hook extending from one end of the body. A stud with a tapered knob on its outer end extends outwardly from the other end of the retaining member body. The size and configuration of the knob and stud enable them to be tightly retained within an end portion of the hollow tubing that is stretchingly installed thereover. A surgical tube connector for joining a pair of hollow elastic surgical tube members having an elongated stud with tapered knobs at each end in which the stud and knobs are dimensioned for tight fitting containment within the end portions of the hollow tube members stretchingly installed thereover.

One of the problems that surgeons face today is that of the risk of a needle, instrument, or other sharp object penetrating the surgeon's glove resulting in a finger puncture. This problem of damaged surgeon's gloves is of particular interest where surgeries are performed on AIDS or other patients with communicable blood born diseases. Therefore, there is a need for an improved elastic surgical retractor stay that minimizes slippage that can result in puncture of a surgeon's gloves.

Some retractor systems have void spaces or cavities at the distal tissue engaging end portion. This creates an opportunity for foreign matter to be carried to and deposited into the wound site.

BRIEF SUMMARY OF THE INVENTION

The present invention provides an improved design for a surgical elastic stay that offers several benefits over the prior art.

The present invention provides a single molded apparatus for a greater security to the surgeon that the formed needle will not become separated from the elastic body or tail thus dropping into the surgical wound site.

The present invention provides a one-part design that allows autoclaving for sterilization so that the elastic stay can be reused.

With the present invention there is no open tailing tube or cavity at the needle and handle connection area. Thus with the present invention, foreign matter cannot easily be deposited into such a cavity and ultimately into the surgical wound site.

The apparatus of the present invention provides a handle with smooth rounded surfaces which are preferable in the wound area. The apparatus of the present invention is thus less likely to damage surgeons' gloves, of particular importance where surgeries are performed on AIDS or other patients with communicable blood born diseases.

The present invention provides an improved finger grip dimple on opposing sides of the handle. This improved grip prevents slippage of the apparatus through the surgeon's fingers. Slippage can be particularly problematic when the elastic stay is covered with blood. The improved grip lowers the risk of the hook portion of the apparatus of the present invention penetrating the surgeon's glove resulting in a finger puncture.

One embodiment of the apparatus of the present invention provides spaced apart enlarged diameter (e.g., spherically shaped) sections on the elastic member so that it can be used in a wide variety of slot widths.

The present invention thus provides an improved surgical stay apparatus that includes a frame that conforms to a patient's body at a surgical site. The stay includes a handle body having proximal and distal ends.

A hook member having proximal and distal end portions is partially embedded within the handle body. A majority of the hook member is embedded within the handle body, including the proximal end portion thereof so that only a distal hook member extends beyond the distal end of the handle body.

An elastic member extends from the handle, the elastic member having an elongated portion that extends from the distal end of the handle body, a distance much greater than the length of the handle.

The hook member includes an exposed curved hook portion that extends from the distal end portion of the handle body.

The hook is of a configuration and the handle is of a material that enables the handle to hold the hook without pull out during use.

In the preferred embodiment, the handle and elastic member are a one piece molded (e.g., injection molded) structure. In the preferred embodiment, the molding process embeds the hook within the handle body.

The hook member is specially shaped to provide a plurality of sections that are offset from one another. Thus, the hook provides an elongated folded arrangement that defines a solid anchor with the handle body when the handle body is molded about the hook member.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

Figure 7:
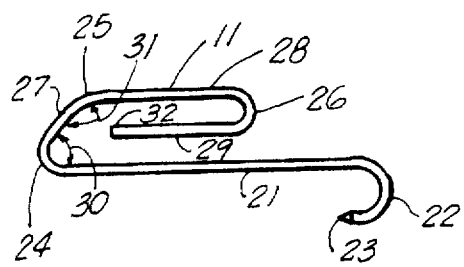
FIG. 7 is a fragmentary side elevational view of the preferred embodiment of the apparatus of the present invention showing the hook member thereof.
Figure 8:
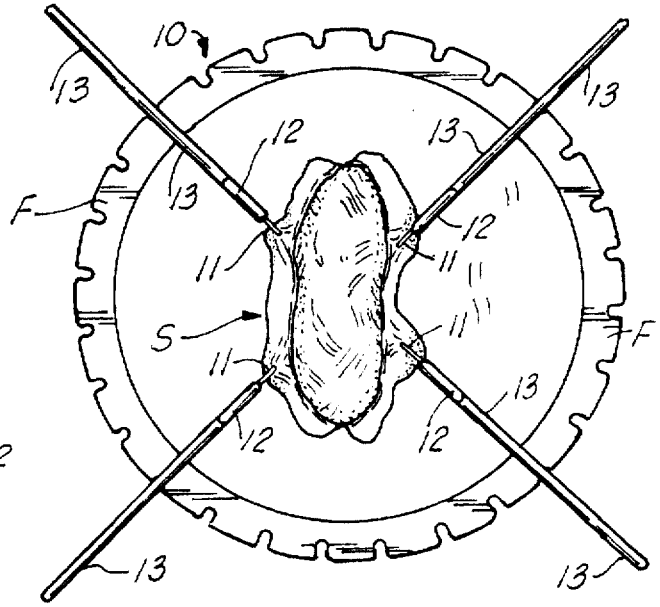
FIG. 8 is a top, plan view of the preferred embodiment of the apparatus of the present invention showing the hook member in phantom lines.

FIGS. 1–4 and 7–8 show the preferred embodiment of the apparatus of the present invention designated generally by the numeral 10. Surgical stay apparatus 10 includes a hook member 11 that is partially embedded within a handle 12. Retractor stay 10 has a distal end 16 and a proximal end 17. Handle 12 is preferably injection molded so that it is a one-piece structure formed simultaneously with elongated elastic member 13. Thus, the combination of handle 12 and elastic member 13 are preferably a one-piece injection molded structure of polymeric plastic material (such as silicon, kraton, or latex, for example), that has an elastic capability. This one piece construction discourages the carriage of foreign matter to the surgical site. It also enables the apparatus 10 of the present invention to be autoclaved. In FIG. 8, surgical stay apparatus 10 is shown in use during a surgical procedure and attached to frame F that surrounds a surgical site S. The use of frame S and its slots for receiving a surgical retractor stay can be seen and is described in prior U.S. Pat. No. 4,430,991, incorporated herein by reference.

The handle 12 includes a pair of opposed concavities or dimples 14, 15. Handle 12 includes an upper portion 18 and a lower portion 19. Tapered section 20 defines a transition in between handle 12 and elongated elastic member 13.

Figure 1:
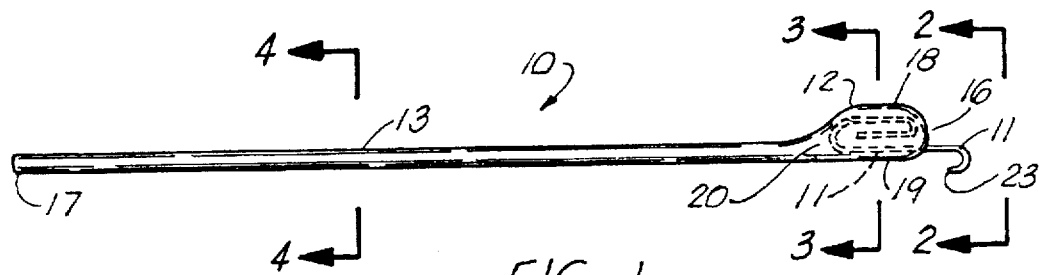
FIG. 1 is a side, elevational view of the preferred embodiment of the apparatus of the present invention showing the embedded hook member in phantom lines.
Figure 2:
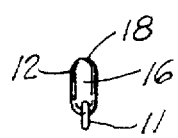
FIG. 2 is an end, elevational view taken along lines 2—2 of FIG. 1.
Figure 3:
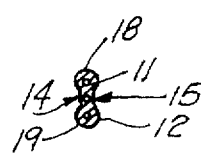
FIG. 3 is a sectional view taken along lines 3—3 of FIG. 1.
Figure 4:
FIG. 4 is a sectional view taken along lines 4—4 of FIG. 1.

Hook member 11 is embedded or molded within handle 12 as shown in FIG. 1. A majority of the length of the hook member 11 is embedded within handle 12 to develop the connection between hook member 11 and handle 12. This ensures that the hook member 11 will not pull out of the handle 12 during use. Preferably, the hook member 11 shown in FIGS. 1 and 6–7 is embedded within the handle 12 by injection molding of the handle, transition section 20, and elongated member 13 at one time while encapsulating the largest part of hook member 11 within handle 12.

The details of construction of hook member 11 are shown in FIG. 7. The hook member 11 includes a large straight section 21 that communicates with a curved distal hook 22. The hook 22 has a sharp point 23 for engaging and holding tissue during use. The curved distal hook 22 is generally semi-circular, extending through an angle of about 180 degrees as shown in FIG. 7.

Bend 24 is provided for connecting straight section 21 with straight section 27. Bend 25 is provided for connecting straight section 27 with straight section 28. Curved arrow 30 in FIG. 7 shows the angular orientation between straight sections 21 and 27, an angle of preferably about 45 degrees. The curved arrow 31 in FIG. 7 defines the angle between straight sections 27 and 28, an angle of preferably about 135 degrees. Bend 26 forms an approximate 180 degree turn that joins straight sections 28 and 29 as shown in FIG. 6. The opposite end of hook member 11 from sharp point 23 is free end portion 32.

Figure 5:
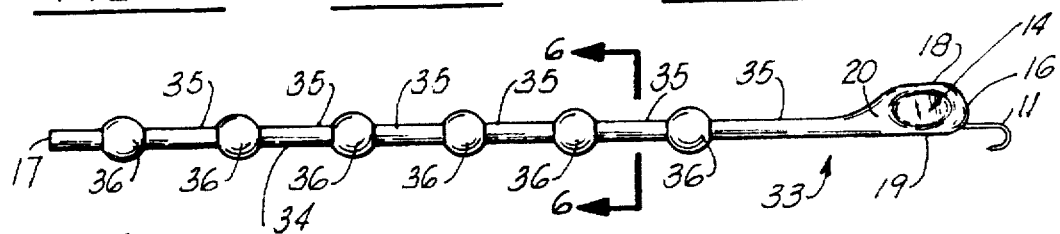
FIG. 5 is a side, elevational view of the second embodiment of the apparatus of the present invention.
Figure 6:
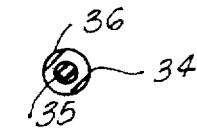
FIG. 6 is sectional view taken along lines 6—6 of FIG. 5.

An alternate embodiment of the apparatus of the present invention is shown in FIGS. 5–6, designated generally by the numeral 33. The surgical retractor stay 33 is identical in construction to surgical retractor stay 10 in the area of handle 12, hook member 11, and tapered section 20. The embodiment of FIGS. 5–6 differs in the construction of the elongated elastic member designated as 34. The elongated elastic member 34 includes uniform diameter cylindrically-shaped smaller diameter portions indicated by the numeral 35 and a plurality of spherically-shaped enlarged diameter sections 36. As with the preferred embodiment, handle 12, tapered section 20 and elongated elastic member 34 can be a one piece, integral molded structure (e.g., injection molded).

The configuration of elongated elastic member 34 shown in FIGS. 5–6 enables the surgical retractor stay 33 to be used in retractors not using the slot detail described in prior U.S. Pat. Nos. 4,274,398 and 4,434,791, each of which is incorporated herein by reference. In those patented retractor systems, the slot configuration relies primarily on a jamming of the tail of the stay tubing into the slot. The surgical retractor stay 33 is injection molded to provide the configuration shown in FIGS. 5–6 and can be used in a wide variety of slot widths.

The following table lists the parts numbers and parts descriptions as used herein and in the drawings attached hereto.

PARTS LIST

| Part Number | Description |
| --- | --- |
| 10 | surgical retractor stay |
| 11 | hook |
| 12 | handle |
| 13 | elongated elastic member |
| 14 | concavity |
| 15 | concavity |
| 16 | distal end |
| 17 | proximal end |
| 18 | upper portion |
| 19 | lower portion |
| 20 | tapered section |
| 21 | large straight section |
| 22 | curved distal hook |
| 23 | sharp point |
| 24 | bend |
| 25 | bend |
| 26 | bend |
| 27 | straight section |
| 28 | straight section |
| 29 | straight section |
| 30 | curved arrow |
| 31 | curved arrow |
| 32 | free end |
| 33 | retractor stay |
| 34 | elongated elastic member |
| 35 | cylindrical section |
| 36 | spherical section |

The foregoing embodiments are presented by way of example only; the scope of the present invention is to be limited only by the following claims.

I claim:

1. A surgical stay apparatus comprising:
 a) frame that conforms to a patient's body at a surgical site;
 b) a one-piece stay that includes a handle body having proximal and distal ends;
 c) a hook member having proximal and distal end portions, the proximal end portion being encapsulated by the handle body, the handle body being molded about a portion of to the hook proximal end portion;
 d) the one-piece stay including an elastic member that extends integrally from the handle, the elastic member having an elongated portion that extends from the distal end of the handle body so that there no detatchable connection at the interface of the handle and elastic member, the elastic member including a proximal end that is connectable to the frame;
 e) the hook member having an exposed curved hook portion extending from the distal end portion of the handle body; and
 f) wherein the hook is of a configuration and the handle and elastic member of a material that enables the handle and elastic member to hold the hook without pull-out or disconnection during use.

2. The surgical retractor stay of claim 1 wherein the hook member proximal end portion includes two offset sections.

3. The surgical retractor stay of claim 1 wherein the hook member proximal end portion includes two offset sections that are generally parallel to one another.

4. The surgical stay apparatus of claim 1 wherein the handle is a molded member that closely conforms to a majority of the hook member.

5. The surgical stay apparatus of claim 1 wherein the hook member includes a wire like portion that has at least one bend that is embedded within the handle.

6. The surgical stay apparatus of claim 1 wherein the hook member includes a wire like portion that has at least two spaced apart bends that are embedded within the handle.

7. The surgical stay apparatus of claim 1 wherein the elastic member is of a generally uniform diameter.

8. The surgical stay apparatus of claim 1 wherein the elastic member has a plurality of spaced apart enlarged diameter sections.

9. The surgical stay apparatus of claim 8 wherein the enlarged diameter sections are spaced at regular intervals along the length of the elastic member.

10. The surgical stay apparatus of claim 1 wherein the hook member has an exposed portion that extends through a bend of about 180°.

11. The surgical stay apparatus of claim 1 wherein the hook member has an embedded portion contained in the handle body that is much longer than the exposed hook portion.

12. The surgical stay apparatus of claim 18 wherein the embedded portion contained in the handle body includes multiple folded portions.

13. The surgical stay apparatus of claim 1 wherein the embedded portion contained in the handle body is an elongated member that is folded, including multiple bends.

14. The surgical stay apparatus of claim 1 wherein the handle has opposed concave dimple portions that are receptive of a user's fingers during use.

15. The surgical stay apparatus of claim 1 wherein the handle has opposed surfaces that are shaped to conform to a user's fingers.

16. A surgical stay apparatus comprising:
 a) a handle body having proximal and distal ends;
 b) a metallic wire hook member having proximal and distal end portions, a majority of the hook member being encapsulated by the handle body, the handle body being molded about a portion of the hook member so that it closely conforms thereto;
 c) an elastic member connected integrally to the handle body so that there is no detatchable connection at the interface of the handle and elastic member, the elastic member having an elongated portion that extends from the distal end of the handle body, the elastic member and the handle body forming a one-piece stay;
 d) the hook member having an exposed curved hook portion extending from the distal end portion of the handle body; and
 e) wherein the hook is of a configuration and the handle and elastic member of a molded material that enables the handle and its elastic member to hold the hook member without pull-out or disconnection during use when the handle is molded to the hook member.

17. The surgical retractor stay of claim 16 wherein the hook member includes a plurality of offset sections.

18. The surgical retractor stay of claim 16 wherein the hook member includes multiple sections that are generally parallel to one another.

19. The surgical stay apparatus of claim 16 wherein the handle is a molded member that closely conforms to and encapsulates a majority of the length of the hook member.

20. The surgical stay apparatus of claim 16 wherein the hook member has at least one bend that is embedded within the handle.

21. The surgical stay apparatus of claim 16 wherein the hook member has at least two spaced apart bends that are embedded within the handle.

22. The surgical stay apparatus of claim 16 wherein the elastic member is of a generally uniform diameter.

23. The surgical stay apparatus of claim 16 wherein the elastic member ha s a plurality of spaced apart enlarged diameter sections.

24. The surgical stay apparatus of claim 23 wherein the enlarged diameter sections are spaced at regular intervals along the length of the elastic member.

25. The surgical stay apparatus of claim 16 wherein the hook has an exposed portion that extends through a bend of about 180°.

26. The surgical stay apparatus of claim 16 wherein the hook member has an embedded portion of a length that is many times longer than the exposed hook portion.

27. The surgical stay apparatus of claim 16 wherein the handle has opposed concave portions that receive the user's fingers during use.

28. The surgical stay apparatus of claim 16 wherein the handle has opposed surfaces that are dished to conform to a user's fingers.

* * * * *